United States Patent
Parce et al.

(10) Patent No.: US 8,980,644 B2
(45) Date of Patent: Mar. 17, 2015

(54) CONTROL OF OPERATION CONDITIONS WITHIN FLUIDIC SYSTEMS

(75) Inventors: J. Wallace Parce, Palo Alto, CA (US); Yung-mae M. Yao, Newtown, MA (US); Donald J. Morrissey, Jr., Redwood City, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 61 days.

(21) Appl. No.: 13/453,829

(22) Filed: Apr. 23, 2012

(65) Prior Publication Data

US 2012/0204964 A1    Aug. 16, 2012

Related U.S. Application Data

(60) Division of application No. 11/165,749, filed on Jun. 23, 2005, now abandoned, which is a continuation of application No. 09/993,385, filed on Nov. 14, 2001, now abandoned, which is a continuation-in-part of application No. 09/919,369, filed on Jul. 31, 2001, now abandoned.

(60) Provisional application No. 60/223,072, filed on Aug. 4, 2000.

(51) Int. Cl.
*G01N 1/10* (2006.01)
*B01L 3/00* (2006.01)
*G01N 27/447* (2006.01)
(Continued)

(52) U.S. Cl.
CPC ......... *B01L 3/5027* (2013.01); *B01L 3/502746* (2013.01); *G01N 27/44791* (2013.01); *G01N 35/08* (2013.01); *B01L 3/502784* (2013.01); *B01L 2200/0673* (2013.01); *B01L 2200/0684* (2013.01); *B01L 2200/141* (2013.01); *B01L 2300/0816* (2013.01); *B01L 2300/105* (2013.01); *B01L 2300/14* (2013.01); *B01L 2400/0415* (2013.01); *B01L 2400/0487* (2013.01); *B01L 2400/049* (2013.01); *B01L 2400/084* (2013.01); *G01N 2035/00237* (2013.01); *G01N 2035/1034* (2013.01)
USPC .............................. 436/180; 422/501; 422/516

(58) Field of Classification Search
CPC ............... B01L 2300/0816; B01L 2400/0487; B01L 2200/027; B01L 3/502715; B01L 3/50273; B01L 3/502746; B01L 3/5027; B01L 2400/084; B01L 9/527; B01L 2400/0406; B01L 2400/082; B01L 3/502784; B01L 3/5025; B01L 2200/0605; B01L 2200/0621; G01N 27/44791; G01N 2035/1034; G01N 35/08; G01N 2035/1062
USPC .................. 422/500–505, 510, 516; 436/180
See application file for complete search history.

(56) References Cited

U.S. PATENT DOCUMENTS 3,479,141 A    11/1969    Smythe et al.
3,699,004 A    10/1972    Skeggs
(Continued)

FOREIGN PATENT DOCUMENTS

DE    101 26 056 A1    1/2002

*Primary Examiner* — Dean Kwak
(74) *Attorney, Agent, or Firm* — Cardinal Law Group

(57) ABSTRACT

The invention provides methods of controlling environmental conditions within a fluidic system, where such environmental conditions can affect the operation of the system in its desired function, and fluidic channels, devices, and systems that are used in practicing these methods. Such methods are generally directed to environmental control fluids, the movement of such fluids through these systems, and the interaction of these fluids with other components of the system, e.g., other fluids or solid components of the system.

10 Claims, 3 Drawing Sheets

(51) Int. Cl.
*G01N 35/08* (2006.01)
*B01L 3/02* (2006.01)
*G01N 35/00* (2006.01)
*G01N 35/10* (2006.01)

(56) References Cited

U.S. PATENT DOCUMENTS

| | | | |
|---|---|---|---|
| 4,853,336 A * | 8/1989 | Saros et al. | 436/53 |
| 5,183,486 A | 2/1993 | Gatten et al. | |
| 5,498,392 A | 3/1996 | Wilding et al. | |
| 5,635,358 A | 6/1997 | Wilding et al. | |
| 5,637,469 A | 6/1997 | Wilding et al. | |
| 5,841,039 A | 11/1998 | Uffenheimer | |
| 5,869,004 A | 2/1999 | Parce et al. | |
| 5,880,071 A | 3/1999 | Parce et al. | |
| 5,885,470 A | 3/1999 | Parce et al. | |
| 5,922,591 A | 7/1999 | Anderson et al. | |
| 5,922,604 A | 7/1999 | Stapleton et al. | |
| 5,942,443 A | 8/1999 | Parce et al. | |
| 5,948,227 A | 9/1999 | Dubrow | |
| 5,955,028 A | 9/1999 | Chow | |
| 5,958,202 A | 9/1999 | Regnier et al. | |
| 5,976,336 A | 11/1999 | Dubrow et al. | |
| 6,042,709 A | 3/2000 | Parce et al. | |
| 6,043,080 A | 3/2000 | Lipshutz et al. | |
| 6,068,752 A | 5/2000 | Dubrow et al. | |
| 6,071,478 A | 6/2000 | Chow | |
| 6,130,098 A | 10/2000 | Handique et al. | |
| 6,149,787 A | 11/2000 | Chow et al. | |
| 6,186,660 B1 | 2/2001 | Kopf-Sill et al. | |
| 6,231,737 B1 | 5/2001 | Ramsey et al. | |
| 6,235,471 B1 * | 5/2001 | Knapp et al. | 435/6.19 |

* cited by examiner

CONTROL OF OPERATION CONDITIONS WITHIN FLUIDIC SYSTEMS

CROSS-REFERENCE TO RELATED APPLICATIONS

This application is a divisional of U.S. patent application Ser. No. 11/165,749, filed Jun. 23, 2005, which is a continuation of U.S. patent application Ser. No. 09/993,385, filed Nov. 14, 2001, which is a continuation-in-part of U.S. patent application Ser. No. 09/919,369, filed Jul. 31, 2001, which claims priority to Provisional Patent Application No. 60/223,072, filed Aug. 4, 2000. The full disclosure of each of these applications is incorporated herein by reference in its entirety for all purposes.

BACKGROUND OF THE INVENTION

Microfluidic systems have advanced to the point where they are beginning to supplant conventional technologies in biological, chemical and biochemical analyses. For example, routine separation based analyses, e.g., nucleic acid separations, protein sizing separations, and the like are now routinely performed in microfluidic systems, e.g., the Agilent 2100 Bioanalyzer and Caliper LabChip® systems. Similarly, high throughput analytical operations, e.g., pharmaceutical screening, high throughput genetic analysis, and the like, are also being transitioned from multi-well formats into microfluidic formats, such as the Caliper HTS sipper chip systems. These microfluidic systems have allowed for increases in throughput while requiring substantially smaller volumes of reagents, smaller equipment footprint, and having more reproducible, automatable, integratable operations.

As with any advancing technology however, the miniaturization of analytical chemistries introduces a number of additional considerations. For example, in conventional scale chemical or biochemical analyses, problems associated with interaction between reagents and reaction vessels are kept to a minimum by virtue of the overwhelming volume of reagents used. Similarly, the nature of the reaction vessels used in conventional technologies, while illustrating the advantages of microfluidic systems, also obviate some of the potential problems of microfluidic systems. For example, because these reaction vessels are typically configured as discrete wells or test tubes, there is little or no issue of interaction between discrete reactions that are being analyzed. Similarly, the open-top nature of these vessels allows the evolution of other interfering components, which is not reasonably practicable in sealed microfluidic channels.

In enclosed microfluidic systems, however, the channel surface to volume ratio is substantially increased over conventional technologies, increasing the effects that those surfaces have on the contents of those channels. Further, because of their enclosed nature, one cannot readily access and control the reactions as they progress through the system. In addition, the sealed nature of these systems can result in the accumulation of evolved gasses from the fluid reagents of a system, where such gases would dissipate into the atmosphere in conventional assay formats.

A number of stop-gap measures have been employed in attempts to address some of these potential problems of microfluidic systems. For example, U.S. Pat. No. 5,880,071 describes methods of reducing effects of electrokinetic biasing of reagents within electrically driven microfluidic channel systems. Similarly, U.S. Pat. No. 6,043,080 to Lip shutz et al., describes the use of gas venting membranes within a miniature chamber, to permit degassing of fluids within a miniature fluidic environment.

SUMMARY OF THE INVENTION

The present invention is generally directed to methods of controlling environmental conditions within a fluidic system, where such environmental conditions can affect the operation of the system in its desired function, and fluidic channels, devices and systems that are used in practicing these methods. Such methods are generally directed to environmental control fluids, the movement of such fluids through these systems, and the interaction of these fluids with other components of the system, e.g., other fluids or solid components of the system.

In a first aspect, the present invention is directed to a method of using an environmental control reagent to maintain optimal conditions within a microfluidic device. The method comprises introducing a volume of a first fluid into a channel segment of a microfluidic device, where the first fluid region comprises an environmental control reagent. A volume of a second fluid is flowed into the channel segment of the microfluidic device immediately before or after the step of flowing the volume of the first fluid through the channel segment.

DETAILED DESCRIPTION OF THE INVENTION

I. General

Figure 1:
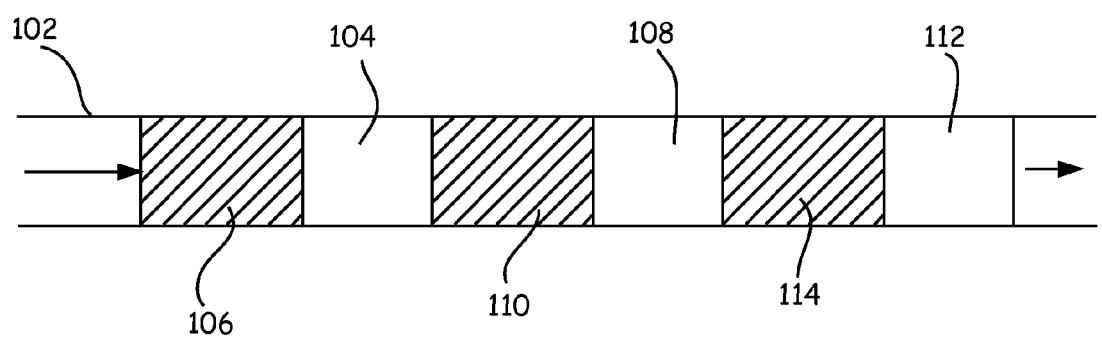
FIG. 1 is a schematic illustration of serial fluid plugs in a fluidic channel, in accordance with certain aspects of the invention.

The present invention generally provides methods for optimizing the operation of microscale channel based systems through the use of environmental or operation control reagents within the fluids that are being transported through the capillary channels. In optionally preferred aspects of the invention, the environmental or operation control reagents are transported in fluid regions that are different from fluid regions that contain the reagents of interest for a given analysis, although such reagents may optionally be disposed within the fluid regions that contain the reagents of interest.

As used herein, the phrase "environmental control reagent" or "operation control reagent" refers to a reagent that typically is not involved directly in the reaction of interest, but instead modifies, controls or provides an indication of the state of the environment within a microscale channel in which a reaction of interest is taking place, so as to control that environment or provide the user with information as to the state of that environment such that external controls may be applied. Some specific and preferred examples of environmental controls include modifying the surface characteristics of the microscale channel, adjusting the viscosity and/or the channel flow resistance, and reducing the potential for gas evolution within the channel. Operation control reagents that are used as indicators or diagnostic reagents typically include, e.g., pH indicators, redox indicators, conductivity indicators, and any of a variety of dyes or labels that indicate the presence or absence of particular species, e.g., proteins, nucleic acids, etc. Because the environmental control reagents are flowed through the microscale channels, either as a constant stream, or in periodic pulses, they continually modify and control the environment within those channels or provide constant indicators as to the state of that environment. This is a particularly useful function where one or more environmental conditions within a microscale channel can change over time or deteriorate with respect to the performance of the reaction of interest.

The methods, devices and systems described herein are particularly useful in performing serially oriented microfluidic analyses, e.g., where analytes are separately and serially introduced into a microscale channel. The serial processing is also multiplexed using multiple separate channels, e.g., where a large number of different analytes are subjected to analysis by serially introducing each into a separate one of multiple parallel channels. In such serially processed analyses, it is often desirable, although not always necessary, to space serially introduced analytes from each other. This is primarily to provide an ease of identification of the different analyte regions within a channel, as well as preventing intermixing of analytes and its potential deleterious effects on the analysis being carried out. These spacer fluid regions are ideal vehicles for the environmental control reagents described herein. In particular, conditions for a given analytical reaction can be optimized without having to account for the presence of the environmental control reagent within the reaction fluid region. Alternatively, a wide variety of different analytes can be tested without having to mix them with these environmental control reagents.

FIG. 1 is a schematic illustration of a serial process analysis that includes multiple reaction fluid regions interspersed with spacer fluid regions that include environmental control reagents. Specifically, reaction fluid regions 104, 108 and 112 are flowed through a microscale channel segment 102. Spacer fluid regions 106, 110 and 114, which include the environmental control reagents, are interspersed between the reaction fluid regions. The spacer fluid regions 106, 110 and 114 include the environmental control reagents as described herein. Although the reaction fluid regions optionally include the environmental control reagents, in preferred aspects the environmental control reagents are primarily contained within the spacer fluid regions. This allows the use of a single source of environmental control reagents, e.g., in a spacer fluid reservoir, rather than requiring mixing of each of the different reaction fluids with those reagents. Additionally, to the extent environmental control reagents might have any effect on the reactions that are being carried out in the reaction fluid regions, they are kept substantially separated. Further, as each spacer fluid region passes through the microscale channel segment, it performs the particular function or functions for which the reagent is intended. In this manner, the spacer plugs perform somewhat of a "housekeeping" function in the microfluidic channel systems.

In certain preferred aspects, the environmental control reagent is flowed through the channel segment immediately following each region of reaction fluid, e.g., such that the fluid region containing the environmental control reagent(s) are interspersed among reaction regions. In certain aspects, the environmental control reagent region is adjacent to and abutting the reaction fluid region, to optimize the environmental control function that those reagents perform. However, in those instances where environmental control functions are not necessary on as routine a basis, the period between environmental control reagent additions can be increased, e.g., after 2, 5, 10 or even 20 or more reaction fluid regions, and their optionally associated spacer fluid regions, have passed through the particular channel segment. Conversely, in some cases, an environmental control reagent may be transported through a channel only once or a few times for the lifetime use of a given channel structure and may increase the useful lifetime of a channel network.

II. Surface Modifying Reagents

As noted above, one exemplary environmental control reagent type is a channel surface modifying reagent. In microscale fluidic systems, the nature of the surface of the microscale channel through which materials are being transported can have a significant effect on the operations that are being performed. For example, surfaces can have properties, e.g., surface charges, hydrophobicity, etc., which promotes the sticking of proteins, cells or other reaction materials to those surfaces. This accumulation of material can subsequently interfere with material flowing or other aspects of a reaction of interest. Similarly, in electrically driven microscale channel systems, the existence of charged functional groups on the channel surface can give rise to electrokinetic movement of fluids within channels, where such movement may be more or less desired.

Accordingly, in many microscale fluidic systems it is desirable to treat the surfaces of the channels to mask unfavorable characteristics or provide or accentuate favorable characteristics. Previously, such surface treatments have focused upon pretreating the channel surfaces through coating processes that involved complex chemical treatments to covalently attach chemical modifying agents to those channel surfaces. In certain applications, e.g., where a channel is used a single time, dynamic coating materials have been described, where a solution of the surface modifying agent is disposed within the channel in order to perform the analysis of interest. While these dynamic coatings are useful in a variety of applications, e.g., where the entire channel segment where the analysis is being performed is filled with the dynamic coating material, their non-permanent nature can be a significant drawback to their use in a number of other applications, e.g., applications where such materials can adversely affect the reaction of interest, as the channel surface properties will change over time as the dynamic coatings are washed from the channel surfaces.

It is these latter situations that are particularly advantageously addressed by the methods of the present invention. Specifically, in applications where one is introducing reaction fluid regions into a microscale channel, surface modifying reagents can be introduced into the channel in a separate fluid region that is flowed through the channel before and/or after the reaction fluid region. This can be repeated each time a new reaction fluid region is introduced into the microscale channel segment or at pre-selected intervals, e.g., regularly spaced intervals. As these spacer fluid regions or plugs flow through the channel, they continually coat or re-coat the surface of the channels for a following reaction fluid region.

A wide variety of different materials are useful as surface modification reagents in accordance with the present invention. For example, as noted above, dynamic coatings that typically comprise surface adsorbing polymer solutions are used as the surface modifying reagent. Examples of such polymer solutions include linear, e.g., non-crosslinked cellulose polymers, agarose polymers, acrylic polymers, e.g., polyacrylamides, and the like. Particularly preferred polymers include linear polyacrylamide polymers, and more particularly linear polydimethylacrylamide polymers (PDMA) and copolymers of these, e.g., PDMA co-acrylic acid polymers as described in U.S. Pat. No. 5,948,227, which is incorporated herein by reference in its entirety for all purposes, monovalent or bivalent compounds that interact with the surface and present different environments to the fluids within the microchannel, e.g., charged groups, hydrophobic moieties, affinity binding moieties, or the like, for use in chromatographic analyses, and the like. A variety of these latter reagents have been described in detail in the art, and could be readily employed in the present invention.

In accordance with this aspect of the invention and with reference to FIG. 1, the surface modifying reagent is provided in a first fluid region that is transported through a particular microscale channel, whereupon the reagent within the first fluid region modifies the surface of the channel. A second fluid region is preferably introduced into the channel following the first fluid region. As the channel surfaces have been previously modified, the influence of those channel surfaces on the reaction is controlled as desired, e.g., minimized, reduced, increased, or otherwise altered for desired effect. In preferred aspects, an additional first fluid region, e.g., containing the surface modifying reagent, is then transported through the channel after the reaction fluid region, to re-coat the channel surfaces. This ensures a consistent level of environmental control among different, serially introduced reaction fluid mixtures.

In a closely related aspect, the environmental control reagents of the invention can be used to counteract build-up of other reagents within a microscale channel by performing cleaning functions within the channel. For example, as noted above, microscale channels, and particularly uncoated microscale channels are very susceptible to deposition and accumulation of material within a flowing system, e.g., as a result of the surface charge or hydrophobicity of the channel surface. Such accumulation can affect the continued operation of a microfluidic system by affecting the concentration of reagents, interfering with detection techniques, etc. Accordingly, in accordance with the present invention, environmental control reagents that are flowed through the channels of the device include "cleaning" agents to remove any accumulated material from channel walls. In its simplest form, such cleaning agents include acids (e.g., HCl), bases (e.g., NaOH), detergents, high salt solutions (NaCl, $NH_4SO_4$, and the like), zwitterionic solutions, e.g., amino acid solutions, nondetergent sulfobetaine (NDSB), and others. Acid or base solutions are typically used at concentrations of greater than 1 mM and preferably greater than about 10 mM, and in some cases greater than 50 mM. In such cases, the environmental control reagents may be separated from sample material containing fluids by a strongly buffered spacer fluid region, e.g., to avoid damaging the sample material. Salt concentrations will generally vary depending upon the nature of the cleaning operation to be carried out and may be in excess of 10 mM and often in excess of 20 or even 50 mM. Similarly, in the case of detergents, a variety of detergents are commercially available and may be employed as desired as an environmental control reagent.

III. Viscosity/Flow Resistance Adjusting Reagents

Environmental control, as used in conjunction with the present invention may also include control of the overall or average fluidic characteristics of a microscale channel or channel network. For example, in pressure driven fluidic systems, e.g., systems where fluid flow is controlled by application of pressure differentials across channels, the rate of flow within channels is dictated, at least in part, by the level of flow resistance within a particular channel. Flow resistance of a channel can be manipulated by adjusting the structural characteristics of the channel, e.g., its length, width and or depth. However, such manipulations are typically carried out at the time of manufacturing of the channel system and are not readily altered.

Flow resistance can also be altered by altering the characteristics of the fluid flowing through the channels. In particular, by adjusting the viscosity of fluids flowing through channels, one can alter the overall flow resistance of those fluids. In accordance with the present invention, certain fluid regions, e.g., spacer fluid regions, can be viscosity adjusted to achieve an overall change in flow resistance through the channel. Implicit in this description is the optional situation where certain fluid regions are not adjusted for viscosity. This can result from an inability to practically adjust viscosity in some of the fluids, due to their numbers, etc., or can be a result of negative interactions between the viscosity adjusting reagents and those other fluids, e.g., reaction components.

A variety of viscosity adjusting reagents may be used in accordance with the present invention, including polymeric reagents, e.g., cellulose, agarose, gelatin, polyacrylamides, i.e., PDMA and co-polymers thereof, PEGs and other polyalcohols, Ficoll, hydrogels, and the like.

IV. Reagents for Controlling Gas Evolution

Another environmental characteristic that can pose potential problems in microfluidic channel systems, and for which the present invention is particularly suited is the variation in dissolved gases within fluids flowing through the channels of the system. In particular, where fluids in microfluidic systems have the potential to evolve dissolved gases, such gases can create substantial problems in microscale channels, including blocking or otherwise restricting flows in channel networks, which can substantially disrupt the efficient operation of those systems. In analytical reactions, the potential for gas evolution is increased where, as in many bioanalytical operations, temperatures are maintained at elevated levels to optimize assay conditions. Similarly, many microfluidic operations involve the use of pressure gradients to manipulate fluids within microscale channel networks. Substantial changes in pressures can lead to outgassing within the channel system. For example, often fluid flow is driven by an applied vacuum, where the pressure drop across the channel network can result in substantial degassing of fluids within the channel networks, where those fluids are sufficiently saturated.

In accordance with the present invention, an environmental control reagent comprises a fluid reagent that is capable of controlling dissolved gas levels within the channel system at levels that do not result in gas evolution within the channels under the conditions of operation. In the simplest aspect, the environmental control reagent in this context is a fluid reagent, e.g., buffer, water, etc., that has a dissolved gas level that is far below the level where gas evolution would be expected in the operation that is being carried out, e.g., at the temperatures and pressures or vacuums involved within the microscale channel systems. Typically, this gas control fluid also has a dissolved gas level that is sufficiently below that of most, if not all of the other fluids that are used in the particular analytical operation, e.g., the reaction fluids, spacer fluids, etc. such that when all of the fluids are mixed, the resulting solution will not evolve gas under the operating conditions of the particular operation.

Because the gas control fluid has such a low level of dissolved gas, it can serve to scavenge excess dissolved gases from the other fluid regions within the channel networks, e.g., the reaction fluid regions, where a degassing operation may not have been reasonably practicable and as a result may have dissolved gas levels that could result in gas evolution within the microscale channel system. In particular, for many operations, e.g., high throughput analytical operations, it is not reasonably practicable to de-gas all of the different sample materials that one is analyzing. Further, in many cases, sample materials are subjected to numerous in-process, but out-of-channel manipulations, e.g., dilutions, mixing, etc. which would effectively negate any attempts at degassing. By maintaining certain fluids within a channel system at dissolved gas levels that are well below saturation, one can balance the effects of higher gas concentrations in other fluids used in the operation. As used herein, the term "saturation" refers to the gas saturation point of a given fluid under the then current conditions within a microscale channel. As a result, the saturation point, or gas solubility, of a particular fluid at one temperature and pressure will be different from the saturation point of the fluid at another temperature and/or pressure.

The reduced level of dissolved gas within the gas control reagents, as described herein, is generally dependent upon the particular operation that is to be carried out, rather than being an absolute characteristic. In particular, where a desired operation is to be carried out within a microchannel structure at lower temperatures, higher absolute concentrations or levels of dissolved gas can be tolerated without evolution. Conversely, where a particular operation is carried out at higher temperatures, lower dissolved gas concentrations are tolerated. Similarly, where negative pressures are applied to fluids within a channel, e.g., as compared to ambient pressure of the fluids prior to their introduction into the channel system, it is generally required that such fluids have lower dissolved gas concentrations in order to avoid outgas sing within the channels. Conversely, positively pressurized channels are generally capable of supporting fluids with higher dissolved gas concentrations.

From the particular conditions of a given operation, one can readily determine the level of acceptable dissolved gas, in order to avoid any problems associated with gas evolution within the channels, e.g., bubble formation. For example, where one knows the temperature at which the fluid is maintained within the channel system, the amount of dissolved gas in some of the fluid reagents, and the amount of applied vacuum in a given channel, one can determine the acceptable level of dissolved gas within a spacer fluid, as well as the relative amount of that spacer fluid needed, to counter any potential of outgassing within the channel. Specifically, one can provide a sufficient amount of a spacer fluid within a channel, where that spacer fluid has a sufficiently low level of dissolved gas, such that any excessive gas concentrations of any of the remaining fluid reagents is absorbable by the spacer fluids without outgassing under the conditions of the operation.

By way of example, where a microfluidic channel network is operated at −2 psi vacuum to cause fluid flow, while the device and all of the reagents are at room temperature, and where the environmental control reagent makes up 40% of the overall fluid volume within the channels of the device, then the environmental control reagent must be at or below 75% saturation with air at room temperature and 1 atmosphere pressure.

Typically, the gas control reagents are only required to be at a saturation level that is at or below that necessary to prevent outgassing of a given system under that system's operating conditions. In accordance with this principle, the degassing fluid need only have somewhat less. However, in general, this results in the gas control reagents having a dissolved gas concentration that is less than 90% of the saturation concentration for any portion of the operation that is to be carried out within the microscale channel system. In preferred aspects, the gas control reagent has a dissolved gas concentration that is less than 80%, more preferably, less than 60%, more preferably, less than 50%, and often less than 40%, 30% or even 20% of the saturation level of dissolved gas in any portion of the operation being carried out.

Although described above in terms of the use of a degassing reagent or fluid within a microfluidic channel system, it is also an aspect of the invention to operate microfluidic systems under conditions that prevent such outgassing, e.g., using any or all fluids within the channel network to prevent outgas sing. In particular, as noted above, the conditions which prevent outgas sing will generally depend upon other conditions of the system, e.g., the applied pressure, the gas saturation level of the fluids within the channels and the gas saturation level of the fluids prior to entering the channel. Gas saturation is highly temperature dependent, e.g., colder fluids can dissolve larger amounts of oxygen than warmer fluids. Similarly, fluids maintained at a lower pressure will evolve more gas than fluids kept at higher pressure. Accordingly, by adjusting one or more of the temperatures of the fluids before and after entering a microfluidic channel network, and/or the pressure or vacuum applied to a system, one can ensure that the system operates under non-out-gassing conditions.

In particularly preferred aspects, the applied pressure is determined by the desired flow rate through the system, e.g., resulting from desired throughput or reaction times. Accordingly, prevention of outgassing is typically a matter of adjusting one or more of the temperatures of the fluids prior to entering the channels and after entering the device. By way of example, a fluid that is maintained at a first temperature, but which is heated upon entering the channel network poses a substantial risk of bubble generation within the channels. This is particularly true where the flow of fluids in the channels is driven by vacuum. Accordingly, to remedy this issue, prior to drawing fluids into the channel network, one can (1) maintain all of the fluids at a temperature that is at or above the temperature of the channel network; (2) elevate the temperature of some portion of fluids (e.g., environmental control/ degassing fluids) above the temperature of the channel network; or (3) cool the channel network to a temperature below that of the outside fluids. Finally, one could also perform any of these adjustments in conjunction with changes in the level of applied pressure to the channel system. As channel temperatures are often optimized for the particular analysis, it is generally preferable that most of the temperature adjustments be made to the fluids prior to their entering the channel networks. This is typically a simple matter of providing a heating element to the sources of these fluids, e.g., multiwell plates, reagent troughs, or the like. Again, as described above, relative temperatures of fluids inside and outside the channel networks are dependent upon the nature of the overall conditions. Typically, however, fluids are maintained at least 1° C. over the temperature of the microscale channel network (also referred to as the chip temperature), and preferably, more than 5° C. This is particularly the case where only a portion of the fluids to be introduced into the chip are provided outside the chip at elevated temperatures. In some cases higher temperature differentials are desirable and may be 10, 20, 30° C. or more, e.g., the temperature of the fluids prior to entering the channel network is 10, 20 or 30° C. higher than the chip temperature. Alternatively or additionally, one can adjust the pressures to which the fluids are subjected so as to prevent bubble formation within a microchannel. For example, in one aspect, one can subject fluids to a low pressure environment, e.g., below ambient, by applying a vacuum to the fluids to degas those fluids prior to introducing them into the channels of the system. Alternatively, or additionally, one can maintain the pressures within the channels at levels that prevent such degassing, e.g., above ambient or the pressure at which the fluids were kept prior to introduction into the channels.

In preferred aspects, because fluids are often flowed through microchannels under an applied vacuum, the latter alternative is not optimally applicable in all situations. As such, where pressure adjustments are used to prevent degassing within the microchannel, it is typically applied as a preloading step, e.g., fluids are subjected to vacuum prior to loading into a channel.

In particularly preferred aspects, the fluids to be introduced are subjected to either one or both of an elevated temperature or reduced pressure environment immediately prior to introducing those fluids into the channels, to prevent re-equilibration of the fluids at atmospheric temperatures, and so as not to necessitate complex sealed bottle systems. As used herein, "immediately prior to introduction" means 5 minutes or less before fluid introduction, preferably 1 minute or less, and often 30 seconds or less. In certain systems, a trough of fluids is continuously recirculated and subjected to elevated temperatures. In the case of subjecting fluids to reduced pressure atmospheres, a variety of different vacuum degassing methods may be employed, including bulk degassing of fluids, e.g., subjecting larger volumes of fluid to negative pressures. However, in the systems described herein, in-line degassing systems are generally preferred. One example of an in-line degassing system, available from Agilent Technologies, applies a negative pressure to one side of a Gore-Tex fabric membrane while the fluid to be degassed is flowed across the other side of the membrane. The system allows gas to pass from the fluid, through the membrane as a result of the applied vacuum, resulting in effective degassing of the fluid in a flowing format. The degassed fluid is then flowed into a trough for sampling, or is delivered directly to a port of a microfluidic device for introduction into the channels of the device.

Although the preferred gas control reagents comprise fluids having sufficiently low dissolved gas concentrations, e.g., buffers, water etc., it will be appreciated that gas absorbing additives may also be used in conjunction with this aspect of the present invention, in order to reduce the potential for outgassing during a given operation. For example, in certain embodiments, it may be useful to employ liquids that have very high oxygen saturation levels, i.e., fluorocarbons and perfluorocarbons.

V. Other Operational Control Reagents

In addition to the environmental control reagents described above, intermediate fluid slugs in microfluidic channels can be put to a variety of other useful functions in microfluidics based analyses. For example, spacer fluid slugs optionally incorporate signaling components, e.g., dyes, labels, etc., so as to provide an indicator component of the spacer slugs versus the sample slugs. Such indicators may be varied in terms of the nature of the label, e.g., in the case of fluorescent labels, via its wavelength of excitation, emission, intensity or the like, to provide the ability to distinguish between spacer slugs at different points in an operation. By way of example, a spacer slug early in an assay run may have a first signaling component, e.g., fluorescing at a first wavelength or combination of wavelengths, whereas later spacer slugs fluoresce at a different wavelength or combination of wavelengths. Depending upon the nature of the spacer slug's label, one can determine where the system is in a given operation, in order to identify intermediate steps in an operation, or match analysis data with exogenously introduced reagent slugs, e.g., allowing identification of the particular reagent slug. Such different labels can be provided by sampling spacer fluids from different sources at different time points in an operation, or by constantly adjusting the signal component make-up of a single source of spacer fluid. For example, a trough of spacer fluid may be slowly, but constantly supplemented with a new labeled signaling component, so as to produce an increasing level of signal in later sampled spacer fluid slugs.

Spacer slugs containing signaling components may also be used as calibrators for detection systems used in conjunction with the devices and methods described herein. In particular, a known concentration of signaling component can be used to set detection system so as to optimally detect assay results.

In addition to the foregoing, signaling components of spacer slugs can be used as indicators or diagnostics of other environmental conditions within a microscale channel system. For example, temperature sensitive signaling components may be used to monitor temperature within such systems over the course of an assay run, while pH sensitive signaling components may be used to indicate intrachannel pH or changes therein. Additionally, ion specific indicators, or generic conductivity indicators may be used. A variety of temperature sensitive signaling components may be used in conjunction with this aspect of the invention, including molecular beacons, self hybridizing nucleic acid sequences that become fluorescent when heated above their melting temperatures. Similarly, pH indicating labels or dyes are widely available from commercial sources, including, e.g., Molecular Probes, Inc. (Eugene, Oreg.). Dyes or labels can also be provided to indicate the level of macromolecular buildup within channels, which buildup might affect the functions of the channels, or their usefulness in a given analysis. Such dyes include protein indicators, nucleic acid indicators, and the like.

VI. Microscale Channels and Systems

As noted repeatedly above, the present invention is most useful in the context of analytical operations that are carried out within a sealed microscale channel environment. In its simplest form, such an environment includes a simple channel, e.g., a capillary, tube or other enclosed conduit through which fluid materials are flowed. However, in preferred aspects, the operations in question are carried out within more complex networks of microscale fluid channels, e.g., in microfluidic devices. Typically, such devices include at least two different microscale channels disposed within the same single body structure. Often, the at least two microchannels will be in fluid communication with each other, e.g., at a channel junction, to form an integrated channel network. In general, microfluidic devices incorporating complex channel geometries have been previously described in, e.g., U.S. Pat. Nos. 5,869,004, 5,942,443, 5,976,336, 6,042,709 and 6,068,752, each of which is incorporated herein by reference in its entirety for all purposes. As used herein, the term microchannel typically refers to a channel conduit that has at least one cross-sectional dimension between 0.1 and 500 µm. Preferably, at least one cross-sectional dimension of a microchannel is between about 1 and about 100 µm.

Figure 2:
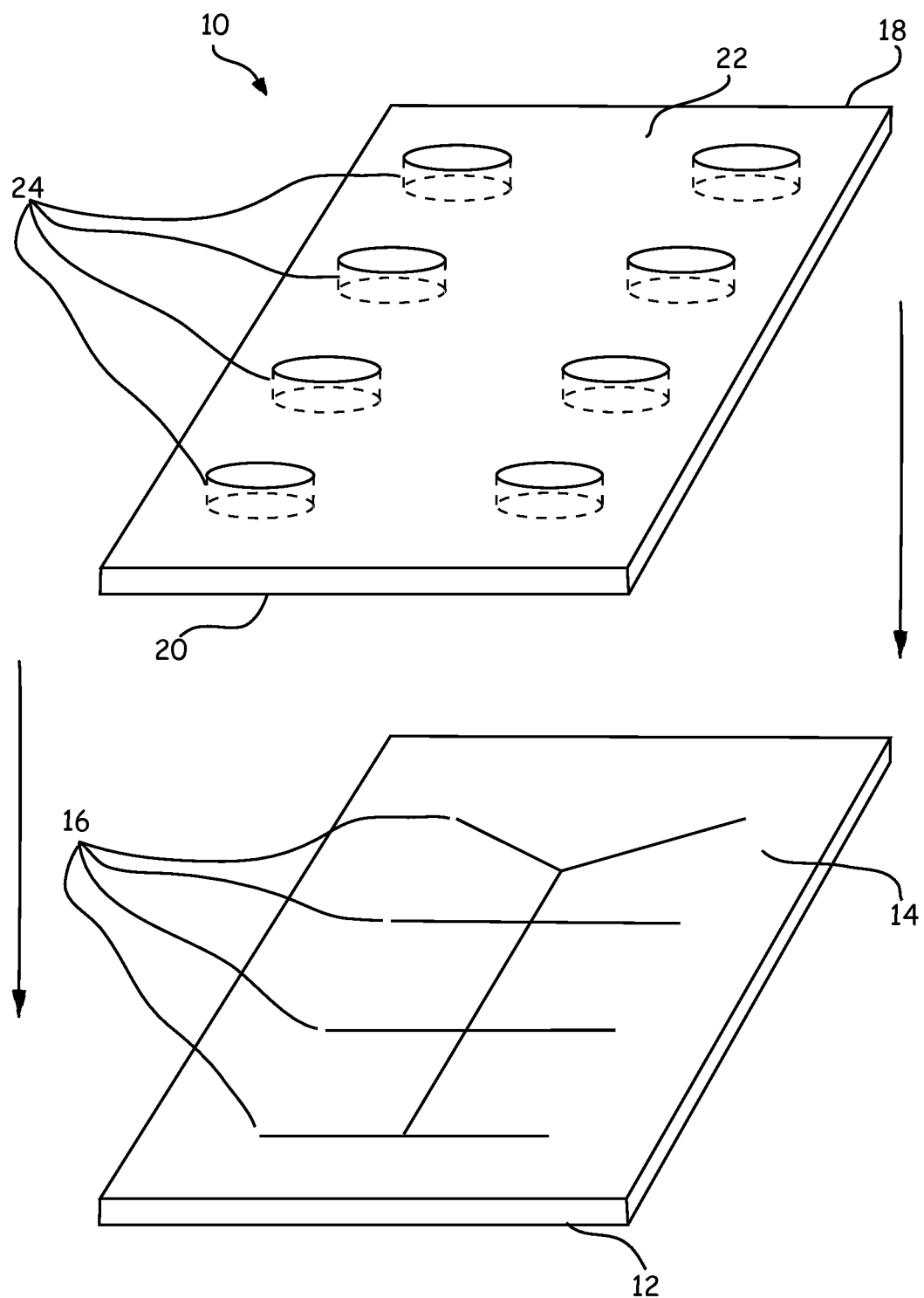
FIG. 2 is a schematic illustration of an exemplary microfluidic device structure.

While microfluidic devices may be fabricated as an aggregate of different parts, e.g., capillaries and chambers, pieced together in a desired orientation, in preferred aspects, such devices are fabricated in a monolithic format, integrated in solid substrates. In particular, microscale channels and channel networks are typically fabricated as grooves into a surface of at least one planar substrate layer. The first substrate layer is then overlaid with a second substrate layer, which is bonded to the first, to seal and enclose the grooves as microscale channels. Reservoirs or access ports are optionally provided in one or both of the substrate layers to provide access to the channels from the outside world. Additional substrate layers are optionally added to increase to the complexity of channel networks that may be produced. Similarly, individual channel networks may be duplicated within one or more different body structures, in order to multiplex operations, and gaining the consequent improvements in throughput. FIG. 2 provides a schematic illustration of the assembly of a layered microfluidic device. As shown, the device 10 includes a lower planar substrate 12 having a plurality of grooves fabricated into its surface. An upper substrate layer 18 is also provided that includes a plurality of apertures disposed through it. The apertures are positioned so as to be in communication with the grooves when the upper layer is placed upon and bonded to the lower substrate. This bonding also seals the grooves as enclosed channels or conduits. Although illustrated as grooves on the lower substrate and apertures through the upper substrate, it will be appreciated that grooves and apertures may be disposed in either and/or both substrates depending upon the desired nature of the finished microfluidic device.

Methods for manufacturing microfluidic devices have been previously described, and include techniques commonly employed in the integrated circuit industries, e.g., photolithography and wet chemical etching, for silica based solid substrates, as well as other well known microfabrication techniques for other materials, e.g., injection molding and embossing techniques for polymer-based materials (see, e.g., U.S. Pat. No. 5,885,470).

Generally, such devices are mounted on an instrument that includes fluid transport systems, as well as detection systems, whereby the instrument interfaces with the microfluidic device to control fluid movement and detect assay results within the channels of the microfluidic device. Such instruments are exemplified by, e.g., the Agilent Technologies 2100 Bioanalyzer and the Caliper Technologies HTS "Sipper" platform, as described at www.calipertech.com and www.Agilent.com, the contents of which are hereby incorporated herein by reference in their entirety for all purposes. Microfluidic devices, methods and systems that include serially introduced fluidic regions, e.g., as described in the preferred embodiments of the invention, are described in substantial detail in U.S. Pat. Nos. 5,942,443, and 6,042,709, each of which is incorporated herein by reference in its entirety for all purposes.

The devices and methods of the invention may be employed in conjunction with appropriate instrumentation depending upon the nature of the analysis that is to be performed. For example, for lower throughput operations, microfluidic devices are readily configured for operation on commercially available controller/detector instrument, e.g., an Agilent 2100 Bioanalyzer that is equipped with at least one pressure/vacuum source. Similarly, higher throughput operations are readily configured to operate on sipper systems that are available from Caliper Technologies Corp. Such systems are described in detail at www.agilent.com and www.calipertech.com and in U.S. Pat. Nos. 5,955,028, 6,042,709 and 6,071,478, each of which is incorporated herein by reference in its entirety for all purposes, as well as the patents described elsewhere herein, and incorporated herein by reference.

VII. EXAMPLES

Figure 3:
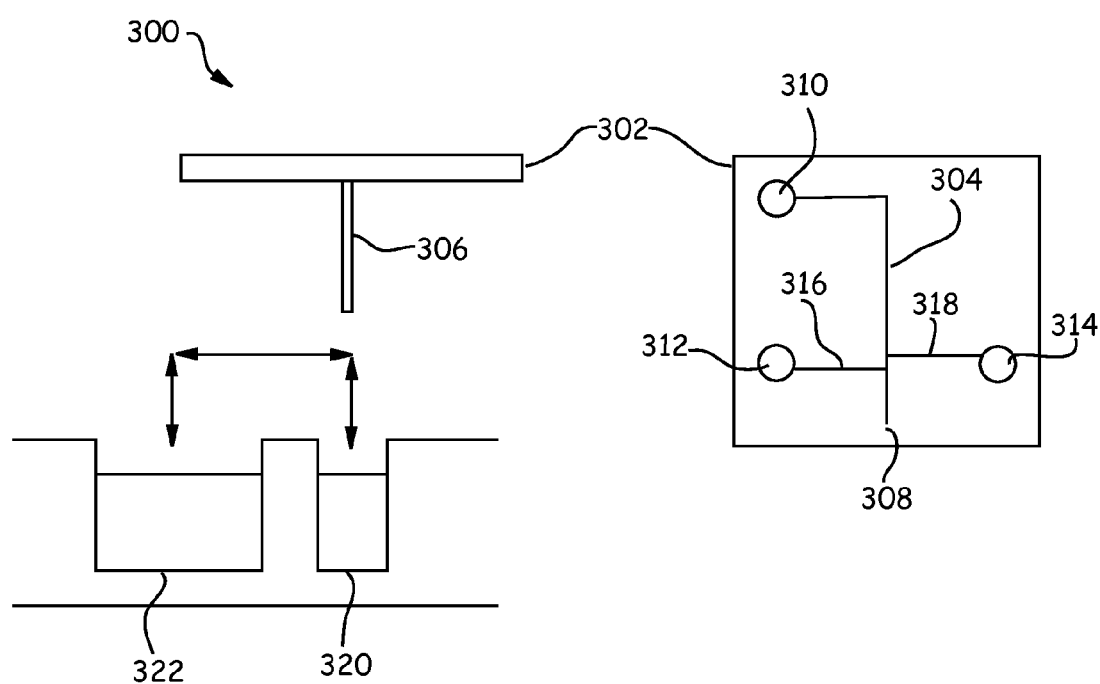
FIG. 3 is a schematic representation of a microfluidic assay device and reagent source used in conjunction with high-throughput applications of the present invention.

The degassing functions of the present invention were modeled and applied in a high-throughput screening system that incorporates a microfluidic channel network. A simplified schematic illustration of the microfluidic device and overall system is shown in FIG. 3. As shown, the microfluidic device 300 includes a planar body structure 302 that includes a channel network disposed within its interior. The channel network includes a main analysis channel 304 that is coupled at one end to an external capillary element 306, via inlet 308.

At the other end, the main channel 304 is fluidly connected to reservoir/port 310. Two side channels 312 and 314 intersect and are in fluid communication with the main channel 304. These channels provide a connection between the main channel 304 and reagent reservoirs 316 and 318, respectively. In the examples described below, sample material is sampled into the main analysis channel through the external capillary 306 by dipping the open end of the capillary into a source of sample material 320 and applying a vacuum at reservoir/port 310. The applied vacuum draws a slug of sample material into the capillary element 306 and moves it into the analysis channel 304. In the system shown, a spacer fluid is introduced after the sample material slug, in order to space the sample material from subsequent sample materials. The spacer buffer is sampled into the system the same way that the sample is drawn in. Specifically, the capillary element is placed into contact with the trough 322 of spacer buffer and a slug of spacer fluid is drawn into the system. Within main channel 304, additional reagents needed for a given analysis are brought into the main channel 304 from the side channels 312 and 314. Movement of reagents into channel 304 from these side channels is driven by the same vacuum used to draw materials in through the capillary element. In the context of the present example, the spacer fluid constituted the degassing fluid.

Degassing parameters were calculated for a system having the attributes described with reference to FIG. 3. In particular, a number of physical and temporal parameters of the operation of a microfluidic device are dictated by the particular analysis to be carried out therein. Those parameters were then used to calculate the maximal allowable level of oxygen within the spacer fluid in order for that fluid to function as a degassing reagent. In order to achieve this oxygen level, therefore, a minimum spacer fluid trough temperature was calculated, e.g., to provide spacer fluid at an acceptable oxygen level. By providing the spacer fluid below maximal oxygen levels, substantial reductions in bubble formation and channel blockage have been observed. Exemplary calculations are provided below.

In one exemplary analysis, sample compounds are sipped for 2 seconds, while spacer fluids are sipped for 1 second. Transit time between the sample well 320 and the spacer fluid trough 322 is 1.5 seconds. For the particular example chip/channel configuration, flow into main channel 304 from the side channels is 50% of the total flow, e.g., 25% from each side channel. The temperature of the sample material is assumed to be room temperature or 22° C., while the device temperature is elevated to 28° C. This elevated temperature is generally desirable to accelerate analysis chemistries within the device. Finally, a vacuum of −0.3 psi is applied to reservoir/port 310 to drive fluid flow through the channels of the device. These parameters were then used to calculate the maximal level of oxygen within the spacer fluid in order to avoid any degassing or bubble formation within the channels of the device, e.g., under the temperature and pressure conditions applied. In carrying out the calculations, two alternate scenarios were assumed. The first case is where a hanging droplet of fluid at the end of the capillary element does not equilibrate with air during the transit time from the sample to the trough. The second case assumes that the droplet becomes fully equilibrated with air during transit. Given that the radius of the water droplet is 0.018 cm and the diffusion constant for oxygen in water is $2 \times 10^{-5}$ cm$^2$/s, giving a diffusion time of 8.1 seconds, the droplet should not equilibrate during a typical transit time, e.g., 1.5 seconds. The calculations are set forth below:

| Input Parameters | | |
| --- | --- | --- |
| Parameter | ID | Value |
| Sample plate sip time (s) | PST | 2 |
| Trough sip time (s) | TST | 1 |
| Sipper transit time (s) | STT | 1.5 |
| Side channel flow (fraction) | SAF | 0.5 |
| Sample plate temperature (° C.) | PT | 22 |
| Chip temperature (° C.) | CT | 28 |
| Applied vacuum (psi) | V | 0.3 |

| Calculated Parameters | | | |
| --- | --- | --- | --- |
| Parameter | ID | Case 1 | Case 2 |
| Sample plate flow (%) | FP | 29.2 | 41.7 |
| Trough flow (fraction) | FT | 20.8 | 8.3 |
| [$O_2$] in plate | OP | $4.17 \times 10^{-3}$ | $4.17 \times 10^{-3}$ |
| [$O_2$] in side channel reservoirs | OS | $3.71 \times 10^{-3}$ | $3.71 \times 10^{-3}$ |
| [$O_2$] allowable in chip | OAC | $3.63 \times 10^{-3}$ | $3.63 \times 10^{-3}$ |
| [$O_2$] allowable in trough | OAT | $2.7 \times 10^{-3}$ | $2.7 \times 10^{-3}$ |
| Minimum trough temp. | MTT | 50 | 94 |
| % Saturation in trough | %O2 | 65 | 12 |

The calculations used to calculate these parameters were as follows:

$$FP1 = [(PST+STT)/(PST+TST+2*STT)][1-SAF]$$

$$FP2 = [(PST+2*STT)/(PST+TST+2*STT)][1-SAF]$$

$$FT1 = [(TST+STT)/(PST+TST+2*STT)][1-SAF]$$

$$FT2 = [(TST/(PST+TST+2*STT)][1-SAF]$$

[$O_2$] in grams of gas/100 grams of water at atmospheric pressure and temperature T is [$O_2$]=13417e-5*(T)–1.301e-8*(T–58.04)^3+4.3 10e-3

$$OAC = OS*((14.7-V)/14.7)$$

$OAT=(OAC-OP*FP(n)-)S*SAF)/FT(n)$ where ($n$) is 1 or 2 depending on the case.

$$MTT=(100-6.628e4*(O_2)+1.5e7(O_2)^2-1.084e9(O_2)^3)/1-5.703e2(O_2)+1.443e5(O_2)^2-2.563e7(O_2)^3+3.298e9(O_2))$$

$$\%O_2=(OAT/OP)*100$$

As noted above, when the trough is maintained above the calculated minimum trough temperature for a given operation, channel plugs resulting from outgassing within channels is substantially reduced.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of using an environmental control reagent to maintain optimal conditions within a microfluidic device, the method comprising:
    selecting a first fluid including an environmental control reagent having a viscosity adjusting reagent;
    introducing a first volume of the first fluid into a channel segment of a microfluidic device, the first volume of the first fluid forming a spacer fluid region completely filling a first length of the channel segment and directly contacting walls of the first length; and
    introducing a volume of a second fluid into the channel segment of the microfluidic device adjacent to and abutting the spacer fluid region, the volume of the second fluid forming a reaction fluid region completely filling a second length of the channel segment and directly contacting walls of the second length, the second fluid comprising a component of a reaction mixture; and
    driving the spacer fluid region and the reaction fluid region through the channel segment;
    wherein the selecting includes selecting the viscosity adjusting reagent to provide a predetermined flow resistance to the driving, wherein viscosity of the first fluid is different than viscosity of the second fluid.

2. The method of claim 1, wherein the first volume of the first fluid is introduced into the channel segment after the volume of the second fluid is introduced into the channel segment.

3. The method of claim 1, wherein the volume of the second fluid is introduced into the channel segment after the first volume of the first fluid is introduced into the channel segment, the method further comprising introducing a second volume of the first fluid into the channel segment after introducing the volume of the second fluid.

4. The method of claim 1, further comprising introducing a volume of a third fluid into the channel segment.

5. The method of claim 1, wherein the second fluid comprises a first test compound.

6. The method of claim 1, wherein the second fluid comprises at least a first component of a biochemical system.

7. The method of claim 1, further comprising introducing a volume of a third fluid between the spacer fluid region and the reaction fluid region, the third fluid comprising a component of a reaction mixture.

8. The method of claim 1, wherein the viscosity adjusting reagent is selected from a group consisting of a polymeric reagent, a polysaccharide, a polysaccharide polymer, a polyacrylamide, gelatin, and a combination thereof.

9. The method of claim 1 further comprising carrying out a reaction of interest in the microfluidic device, wherein the environmental control reagent is a reagent not involved directly in the reaction of interest.

10. The method of claim 9, wherein the reaction of interest is carried out within the channel segment of the microfluidic device.

* * * * *